United States Patent

Pryor

[11] Patent Number: 5,125,607
[45] Date of Patent: Jun. 30, 1992

[54] STABLE SUPPORT STAND ADAPTED FOR FLAT STORAGE

[75] Inventor: John W. Pryor, Oceanside, Calif.

[73] Assignee: Pryor Products, Oceanside, Calif.

[21] Appl. No.: 639,671

[22] Filed: Jan. 8, 1991

[51] Int. Cl.⁵ .............................................. A47G 29/00
[52] U.S. Cl. ..................................... 248/125; 248/129
[58] Field of Search .............. 248/125, 121, 122, 129, 248/417, 406.2; 211/205, 196

[56] References Cited

U.S. PATENT DOCUMENTS

| | | | |
|---|---|---|---|
| 1,832,041 | 11/1931 | Moehler | 248/129 X |
| 1,857,930 | 5/1932 | Altorfer | 248/129 X |
| 2,041,370 | 5/1936 | Pottorff | 248/129 X |
| 3,131,112 | 4/1964 | Abramson | 211/205 X |
| 3,837,611 | 9/1974 | Rhoades | 248/417 |
| 4,113,222 | 9/1978 | Frinzel | 248/125 X |
| 4,315,613 | 2/1982 | Godwin et al. | 248/406.2 |
| 4,332,378 | 6/1982 | Pryor | 248/125 X |
| 4,706,368 | 11/1987 | Crissman, III et al. | 248/122 X |
| 4,733,838 | 3/1988 | van der Lely | 248/122 X |

FOREIGN PATENT DOCUMENTS 2436331  2/1976  Fed. Rep. of Germany ...... 248/125

Primary Examiner—Ramon O. Ramirez
Attorney, Agent, or Firm—Brown, Martin, Haller & McClain

[57] ABSTRACT

A support stand suitable for use in medical or other applications, which can be shipped or stored in a flat configuration. A support base is equipped with several rollers, located generally around the outside perimeter, which serve to support the assembled medical support stand. The depressed inside portion of the base is equipped with a permanently attached base post having a Morse taper or the like. A support post can be quickly assembled to the base with a single bolt by slipping the support post over the base post and tightening the bolt from beneath the base. The use of a Morse taper, a depressed inner portion in the base, and a female support post configuration are improvements that ensure the necessary strength, rigidity, stability and hygiene necessary for a support stand intended for use in medical applications.

11 Claims, 1 Drawing Sheet

STABLE SUPPORT STAND ADAPTED FOR FLAT STORAGE

BACKGROUND OF THE INVENTION

1. Field of the Invention

This invention involves movable, free-standing support apparatus for medical and other applications and, more specifically, involves a very stable support stand adapted for storage and shipment in an efficient flat pack configuration.

2. Description of the Related Art

The mobile support stand is well-known in the art and has been used for many years in the medical and hospital environment. The typical mobile support stand provides a long vertical support post mounted on a broad wheeled base. The support post is often equipped with a variety of mounting means for supporting medical apparatus and therapeutic products. The wheeled base is designed to permit efficient movement from room to room while also providing firm and stable support to the central support post during use. The urgent nature of some medical care introduces a risk of tipping or upsetting of the entire support stand that must be minimized through careful design of the supporting base. Because medical support stands are used in a medical treatment environment, the support stand and related equipment must be easy to clean reliably and to keep hygienic. This is especially true with intravenous (IV) support stands because of the substantial opportunity for spills and contamination of the supporting apparatus.

The design of mobile support stands for use in medical applications is governed by these requirements for stability, mobility, rapid deployment and hygienic maintenance. Unfortunately, these constraints have heretofore led to a number of bulky and cumbersome designs by practitioners in the art. When such a typical mobile support stand design is packed for shipment by the manufacturer, it must either be boxed in a large container with substantial empty space or it must be broken down and laboriously assembled at destination with skilled labor. Both of these options adds to the cost of the support stand.

The bulky and wasteful shipping requirements of the typical factory-assembled medical support stand adds to medical equipment procurement cost in an era when increasing medical costs are anathema. The shipment of a disassembled medical support stand for assembly at destination by untrained personnel is also undesirable because of the risks of improper assembly, which can lead to awkward deployment and physical instability during use in medical emergencies. Accordingly, there is a long felt need for a mobile support stand design that can be packed and shipped in an efficient configuration with minimal wasted space and that can be quickly and reliably assembled at destination by unskilled labor. Such an apparatus must meet all stability, mobility, rapid deployment and hygienic maintenance requirements for medical support stands.

Previous attempts by practitioners in the art to solve this problem have met with limited success. FIG. 1 illustrates three types of post-base joints. Attempts to provide a base having a threaded hole for receiving the central supporting post, illustrated in FIG. 1C, experienced poor stability and insufficient strength at the threaded joint between the parts. With even the most robust of such designs, medical and body fluids can seep into the threaded joint at the base of the support stand where they create a hygienic hazard and cannot be removed without complete disassembly and diligent cleansing.

Other designs employing welded or unistructure joints, where the central post is permanently joined to the supporting base as shown in FIG. 1A, cannot be disassembled for flat packing and must be packed in large bulky containers with substantial wasted space. The need for stability requires the use of a large, heavy wheeled base not readily adaptable for hinging or collapsing.

FIG. 1B illustrates an attempt by the Japanese to solve this problem. Although new to the art, this design, using a base with a tapered hole and an upright support pole with an internal weld nut that is engaged with a bolt and pulled into the hole in the base, has several deficiencies. The center of gravity of the base was elevated to allow enough depth to engage a sufficient length of the support pole for the requisite strength. This raises the center of gravity of the entire support stand, reducing stability. This design also creates a nonhygienic condition where medical and body fluids and debris can accumulate in the recess formed between the support pole and the base.

Other designers presented with the problem of producing a shippable support stand have been unable to discover an acceptable solution. All configurations using a base-post joint known in the prior art fail to meet or exceed the stability, mobility, rapid deployment and hygienic maintenance requirements. These unresolved problems and deficiencies are clearly felt in the art and are solved in the present invention in the manner described below.

SUMMARY OF THE INVENTION

The present invention incorporates several improvements to the typical mobile support stand used in medical and other applications. It is an important feature of the present invention that the center support post is removable from the base so that the two parts can be packed and shipped in an efficient, flat storage configuration. This feature is available without sacrificing the stability, mobility, rapid deployment and hygienic maintenance features required for a mobile support stand used in a medical environment.

The present invention maintains and improves stability by reducing the center of gravity below that of a conventional design. In addition, the present invention uses a base post, having a Morse taper or the like, attached permanently to the base. The support post is adapted to slip down over the base post and is secured with single bolt engaging an internal weld nut. Because the support post fits over the base post rather than into a base cavity, no inaccessible crevices are introduced that may trap medical or body fluids, thereby maintaining the necessary hygienic maintenance conditions. The use of a base post having a Morse taper together with a pull-down bolt engaging a weld nut inside the similarly-tapered support post adds considerable strength to the joint between the support post and the base.

It is an additional feature of the present invention that the support post can be rapidly attached to the base by unskilled labor with a single bolt without looseness or instability caused by inadequate attachment strength. The present invention can be shipped in a flat pack no higher than the length of the base post, which need not exceed 250% of the support post diameter. The foregoing, together with other features and advantages of the present invention will become more apparent when referring to the following specifications, claims and accompanying drawings.

BRIEF DESCRIPTION OF THE DRAWINGS

For a more complete understanding of the present invention, reference is now made to the following detailed description of the embodiment illustrated in the accompanying drawings, wherein.

DESCRIPTION OF THE PREFERRED EMBODIMENT

Figure 1A:
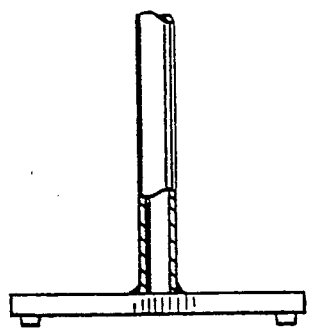
FIG. 1 illustrates existing support stand designs, comprising FIG. 1A showing a welded or unistructural design, FIG. 1B showing the Japanese tapered hole design, and FIG. 1C showing a threaded design.
Figure 1B:
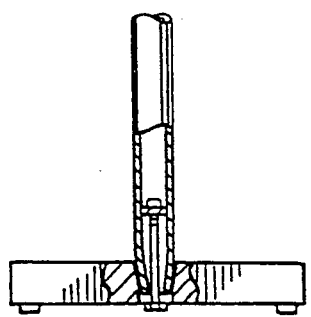
Figure 1C:
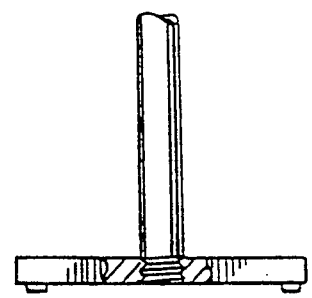
Figure 2:
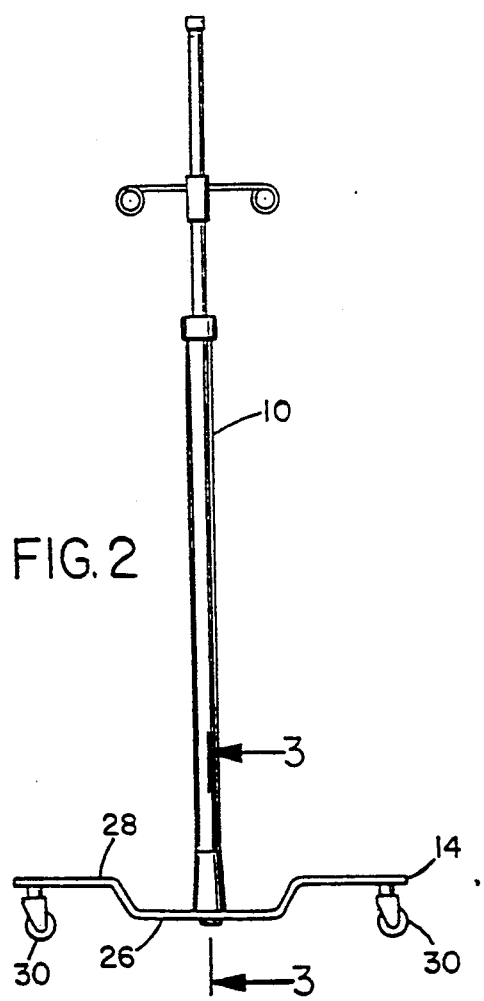
FIG. 2 shows a completely assembled embodiment of the present invention.
Figure 3:
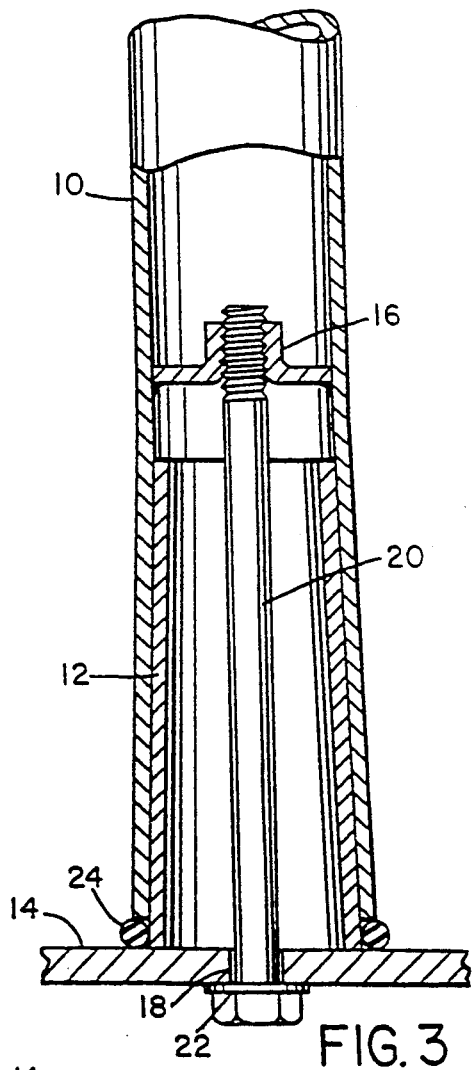
FIG. 3 shows that the post and base joint detail on a section from the FIG. 2 embodiment.

The present invention incorporates several improvements to the typical mobile support stand used in medical and other applications as can be seen by referring to FIG. 2. The removable center support post 10 fits over a mounting post 12 as shown in FIG. 3. Mounting post 12 is welded or otherwise permanently affixed to base 14 and is configured in a Morse taper such that the top of mounting post 12 is of smaller diameter than the bottom. Base 14 can be the star-like design as disclosed in the patent application entitled "Star-Shaped Base for a Support Stand," U.S. application Ser. No. 07/638,753 filed Jan. 8, 1991, which is also owned by the Assignee of this application.

The Morse taper is a standard taper known in the art for use with certain types of small tools and machine parts. Such tools are provided with tapered shanks that fit into spindles or sockets of corresponding taper, thus providing accurate alignment and a degree of frictional resistance for driving the tool. These standard tapers are known in the art as "self-holding" tapers and the Morse taper is the self-holding taper most widely used by American manufacturers.

Because the angle of the Morse taper is only 2° or 3°, the shank of tapered mounting post 12 is so firmly seated in the socket of tapered support post 10 that there is considerable frictional resistance to any force tending to turn or rotate support post 10 relative to mounting post 12. The self-holding Morse taper is distinguished from the "self-releasing" taper used with milling machines and the like, which has a more severe taper permitting easier release.

The Morse taper varies from number 0 to beyond number 10 and is approximately 0.625 inches per foot at any number. For my support stand design, I prefer a Morse taper number 4 or number 5. Morse taper number 4 has a precise taper of 0.6233 inches per foot and Morse taper number 5 has a taper of 0.6315 inches per foot.

I prefer a 2.5 inch or greater base post 12 length for a support post 10 inner diameter of slightly more than one inch. The base post 12 length can be increased without detracting from the necessary strength and stability of assembled medical support stand. I prefer a threaded bolt 20 specification of 5/16-18 UNC or larger.

Referring to FIG. 3, support post 10 is provided with an internal weld 16 nut located at the region between the untapered and tapered section of support post 10. The presence of weld nut 16 at this location acts to strengthen support post 10 against lateral forces.

Base 14 comprises a hole 18 through which a threaded bolt 20 is placed so that bolt 20 threadably engages weld nut 16. Washer 22 provides a bearing surface against which bolt 20 can be turned to tighten support post 10 down onto base post 12. Sealing ring 24 is positioned to seal the region between support post 10 and base 14 when assembly is complete.

Figure 4:
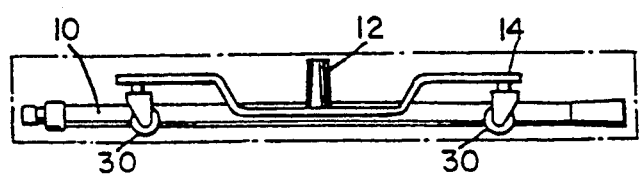
FIG. 4 shows the FIG. 2 embodiment disassembled for shipping.

Referring to FIG. 2, note that base 14 has an inner portion 26 that is disposed at an elevation lower than the outer portion 28 of base 14. This is made possible by the use of rollers 30, which are long enough to hold the entire base 14 off of the floor. The lowered inner portion 26 of base 14 is preferred because of the resulting lower center of gravity and profile of base 14 assembly as seen in FIG. 4. Note that base post 12 is not much longer than rollers 30 and that lowering inner portion 26 of base 14 allows the entire base 14 assembly to be packed in a carton not much higher than the lengths of base post 12 and roller 30.

My invention is not easily disassembled, because of the self-holding nature of the Morse taper, but disassembly can be accomplished by unscrewing threaded bolt 20 and tapping the bolthead with a hammer to jar support post 10 loose from base post 12. Assembly of my invention requires no special skills. The medical support stand assembly is entirely self-aligning and is assembled by turning bolt 20 with a single wrench. The large surface area encompassed by the joint between base post 12 and support post 10 provides the necessary strength and stability for the support stand.

Obviously other embodiments and modifications of the present invention will occur readily to those of ordinary skill in the art in view of these teachings. Therefore, this invention is limited only by the following claims, which include all such obvious embodiments and modifications when viewed in conjunction with the above specification and accompanying drawings.

I claim:

1. A support stand comprising:
  a base having an upper side and a lower side;
  a base post having an upper end and an outer diameter which tapers continuously outwardly from said upper end to a wider lower end, said lower end being attached to said upper side of said base; and
  a support post having a hollow lower end portion for fitting over said base post, said lower end portion having an inside diameter having an inside taper which closely matches the taper of said base post and which tapers continuously between opposite ends of said hollow lower end portion, said inside taper comprising means for tight frictional engagement with the outer taper of said base post to retain said support post on said base post and to resist relative rotation or axial movement between said base and support posts.

2. The support stand of claim 1, additionally comprising a threaded bolt positioned under said base and extending through said base post and wherein said support post comprises a threaded nut affixed internally such that said threaded bolt is rotatably engaged with said threaded nut, whereby rotation of said threaded bolt pulls said support post down onto said base post.

3. The support stand of claim 2 additionally comprising a sealing means disposed at said lower end of said base post for sealing said hollow lower end of said support post when said support post is drawn fully onto said base post.

4. The support stand of claim 3 wherein said outside and inside tapers are Morse tapers.

5. The support stand of claim 4 wherein said base has an inner portion surrounded by an outer portion and said inner portion is disposed below outer portion.

6. The support stand of claim 5 additionally comprising a plurality of rollers attached to the lower side of said outer portion of said base and extending downward to the floor whereby said support stand is supported rollably above the floor.

7. The support stand of claim 4 additionally comprising a plurality of rollers attached to said lower side of said base and extending downward to the floor whereby said support stand is supported rollably above the floor.

8. The support stand of claim 1 wherein said base has an inner portion surrounded by an outer portion and said inner portion is disposed below said outer portion.

9. The support stand of claim 8 additionally comprising a plurality of rollers attached to the lower side of said outer portion of said base and extending downward to the floor whereby said support stand is supported rollably above the floor.

10. The support stand of claim 1 additionally comprising a plurality of rollers attached to said lower side of said base and extending downward to the floor whereby said medical support stand is supported rollably above the floor.

11. The support stand of claim 1 wherein said outside and inside tapers are Morse tapers.

* * * * *